US00PP33224P2

(12) United States Plant Patent
Carter

(10) Patent No.: US PP33,224 P2
(45) Date of Patent: Jun. 29, 2021

(54) ***SALVIA* PLANT NAMED 'SMOKEY JAZZ'**

(50) Latin Name: ***Salvia* x *guaranitica***
Varietal Denomination: Smokey Jazz

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 17/017,592

(22) Filed: Sep. 10, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Susan McCormick Ewoldt
*Assistant Examiner* — Karen M Redden
(74) *Attorney, Agent, or Firm* — Weatherly IP Solutions, LLC; Barbara Campbell

(57) ABSTRACT

A new cultivar of *Salvia* plant named 'Smokey Jazz' that is distinguishable by a compact well-branched upright plant habit, non-spreading root system, dark green leaves, vibrant red-purple flowers which are initiated very quickly and continue from early spring to fall and dark-purple calyces, is disclosed.

2 Drawing Sheets

Genus and species: *Salvia* x *guaranitica*.
Variety denomination: 'Smokey Jazz'.

BACKGROUND

The present disclosure relates to a new and distinct cultivar of *Salvia* plant, also known as a sage, a perennial that is grown for use as an ornamental landscape and container plant. The new variety is known botanically as *Salvia* x *guaranitica* and will be referred to hereinafter by the cultivar name 'Smokey Jazz'.

'Smokey Jazz' was selected in Fall 2018 from a population of seedlings which the inventor raised from seed collected from plants resulting from the controlled hybridization between the female parent plant *Salvia* 'BBSAL09001' (U.S. Plant Pat. No. 30,206) and the male parent plant *Salvia* 'Rhythm and Blues' (U.S. Plant Pat. No. 29,585). The hybridization and selection were carried out at a nursery in Elk, Calif.

'Smokey Jazz' was selected by the inventor for its combination of unusual flower color, very long bloom period, deep green foliage and a naturally compact and branching plant habit.

'Smokey Jazz' was first asexually propagated in Summer 2019 in a greenhouse at a nursery in Elk, Calif. using softwood tip cuttings. 'Smokey Jazz' is stable and reproduces true to type in during successive cycles of asexual propagation via softwood tip cuttings.

SUMMARY

The following traits have been repeatedly observed and represent the distinguishing characteristics of 'Smokey Jazz'. 'Smokey Jazz' has not been tested under all possible conditions and phenotypic differences may be observed with variations in environmental, climatic, and cultural conditions, without however, any variance in genotype.

1. 'Smokey Jazz' exhibits a compact well-branched upright plant habit.

2. 'Smokey Jazz' is non-spreading in the landscape.
3. The flowers of 'Smokey Jazz' are vibrant red-purple in color.
4. 'Smokey Jazz' flowers very rapidly. Freshly rooted cuttings of 'Smokey Jazz' may initiate flower buds in 2 to 3 weeks after rooting.
5. Fully-grown plants of 'Smokey Jazz' will be in full flower within 10 to 12 weeks of planting a rooted cutting.
6. The calyces of the flowers of 'Smokey Jazz' are dark purple in color.
7. 'Smokey Jazz' produces new flowering stems continuously from spring to fall.
8. The foliage of 'Smokey Jazz' is dark green in color at all stages of growth.

DESCRIPTION OF THE PHOTOGRAPHS

The accompanying color photographs illustrate the overall appearance of the new *Salvia* cultivar 'Smokey Jazz' showing the colors as true as reasonably possible to obtain in colored reproductions of this type. The photographs were taken in Summer 2020 from five-month-old plants grown outdoors in Oxnard, Calif. The plants had received one pinch after initial cutting establishment. Colors in the photographs may differ from the color values cited in the detailed botanical description, which more accurately describes the actual colors of the new variety 'Smokey Jazz'.

DESCRIPTION OF THE NEW VARIETY

Figure 1:
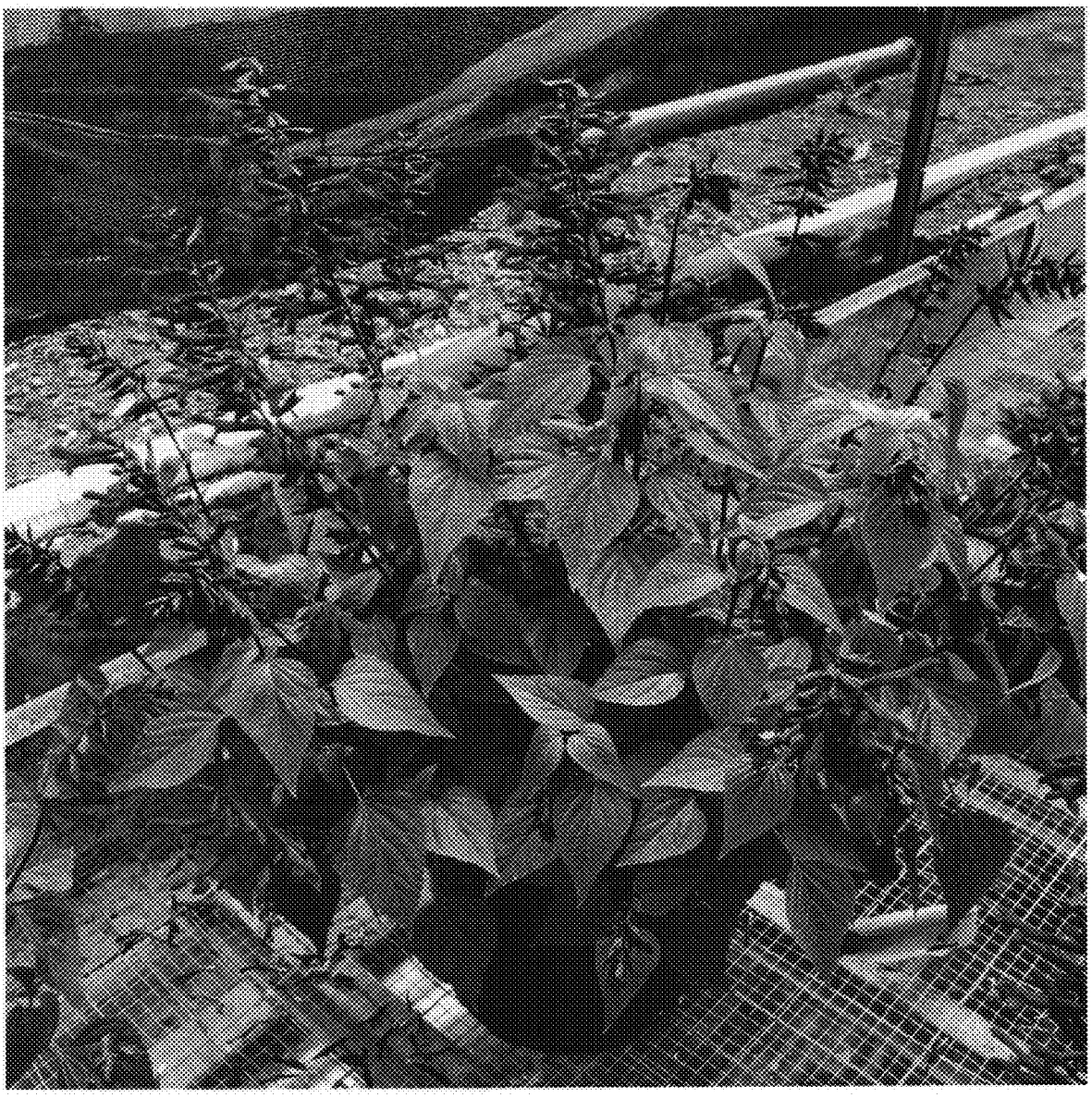
FIG. 1 depicts an entire plant of 'Smokey Jazz' in bud and flower.
Figure 2:
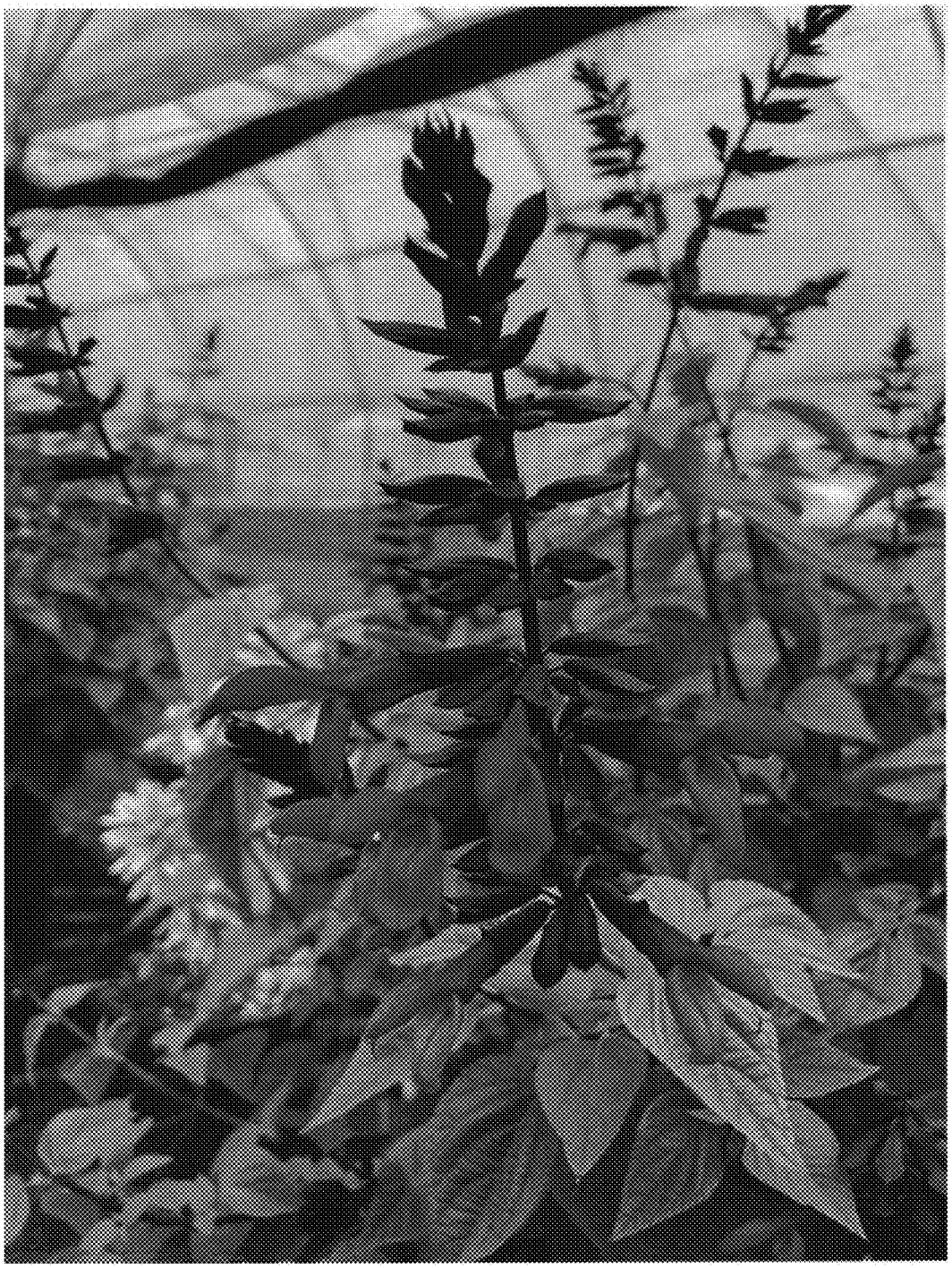
FIG. 2 depicts a close-up view of the inflorescence of 'Smokey Jazz'.

The following detailed descriptions set forth the distinctive characteristics of 'Smokey Jazz'. Observations, measurements, values, and comparisons were collected in August 2020 in Santa Barbara, Calif. from five-month old plants grown in a 2-gallon container outdoors in full sun. Color determinations have been made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—X *guaranitica*.

*Common name*.—Sage.

Parentage:

*Female parent*.—*Salvia* 'BBSAL09001' (U.S. Plant Pat. No. 30,206).

*Male parent*.—*Salvia* 'Rhythm and Blues' Blues' (U.S. Plant Pat. No. 29,585).

Plant:

*Propagation method*.—Softwood tip cuttings.

*Rooting system*.—Fine and fibrous and non-spreading.

*Vigor*.—Moderate vigor.

*Time to develop roots*.—7 to 10 days are needed for a cutting to develop roots at recommended rooting temperature of 20° to 22° Centigrade.

*Crop time*.—Approximately 10 to 12 weeks are required to produce a budded and flowering plant in a one-gallon container from a rooted cutting.

*Suggested container sizes*.—Quart, 1-gallon, 2-gallons.

*Use*.—Ornamental for use as a landscape plant or container plant.

*Type*.—Perennial in USDA Zone 7, annual in colder regions.

*Overall dimensions*.—After five month's growth in a 1-gallon container, 50 cm to 55 cm in height, including the inflorescence, and 25 cm to 30 cm in width. A mature plant of 'Smokey Jazz' in the landscape will achieve a height of 75 cm and a spread of 50 cm.

*Cultural requirements*.—Grow in full sun with moderate water and well-draining soil.

*Hardiness*.—USDA Zone 7.

*Form*.—Bush.

*Growth habit*.—Compact.

*Blooming season*.—From early spring until fall, or until first frost in colder regions.

*Lastingness of blooms*.—Inflorescence has some flower for 14 days, individual flowers last for 2 to 3 days.

Stem:

*Initial stem length* (*below first pinch or stop*).—10 cm.

*Width*.—5 mm to 7 mm.

*Color*.—146D.

*Shape*.—Square, edges rounded.

*Texture*.—Suffruticose.

Branches:

*Quantity*.—12 to 15 branches emerge from initial stem after pinching or stopping.

*Length* (*to base of raceme*).—18 cm to 25 cm.

*Width*.—4 mm.

*Internode length*.—1.5 cm to 2.0 cm.

*Color*.—146D (branch stems within foliage canopy), becoming N186B in full light and towards the inflorescence.

*Shape*.—Square.

*Texture*.—Smooth.

Leaves:

*Type, arrangement*.—Simple, opposite.

*Attachment*.—Petiolate.

*Quantity per branch*.—4 to 6 pairs.

*Shape*.—Deltoid.

*Length*.—5.5 cm.

*Width*.—4 cm.

*Margin*.—Weakly undulating, regularly dentate. Teeth 3 mm apart, 1.5 mm in depth.

*Venation*.—Pinnate. Veins (adaxial surface): Depressed, color as leaf except midrib, 160C. Veins (abaxial surface): Raised, color N186C.

*Texture* (*both surfaces*).—Pubescent, hairs very fine, color hard to match, lighter than N187D.

*Color*.—Adaxial surface: 137A. Abaxial surface: 137C.

*Apex*.—Acute.

*Base*.—Hastate.

*Fragrance*.—Pleasant sage fragrance when rubbed.

*Stipules*.—Present in pairs at each leaf axil. Small, sessile, elliptic, up to 5 mm in length, 2 mm to 3 mm in width. Veins not evident. Color, apex, base descriptors as leaves.

Petiole:

*Shape*.—Terete, adaxial channel.

*Length*.—2.0 cm to 2.5 cm.

*Width*.—1.5 mm.

*Texture*.—Puberulent.

*Color*.—N186C.

Peduncle:

*Length* (*from uppermost leaf pair to first whorl*).—4 cm to 5 cm.

*Length* (*from first whorl to uppermost whorl*).—17 cm to 20 cm.

*Shape*.—Square.

*Width*.—4 mm to 5 mm.

*Texture*.—Puberulent.

*Color*.—N186C.

Inflorescence:

*Type*.—Terminal raceme.

*Length*.—13 cm to 15 cm.

*Diameter*.—7 cm to 8 cm.

*Flower arrangement*.—Flowers are arranged in whorls.

*Quantity of flowers*.—75 flowers on average, consisting of 4 to 6 flowers per whorl and 13 to 17 whorls per raceme.

*Distance between whorls*.—1.0 cm. to 1.5 cm.

*Flowering season*.—Year-round in Southern California and spring to summer elsewhere.

*Lastingness of the flowers* (*on the plant*).—From 8 days in spring to 3 days in Summer.

Pedicel:

*Length*.—5 cm.

*Width*.—1 mm.

*Texture*.—Puberulent.

*Color*.—N186B.

Calyx:

*Shape*.—Campanulate, flared toward the apex.

*Length*.—16 mm.

*Width*.—5 mm.

Sepals:

*Quantity*.—2, one upper, one lower, substantially longitudinally fused.

*Length*.—16 mm, of which 4 mm are free.

*Width*.—8 mm when flattened.

*Shape*.—Boat shaped.

*Apex*.—Acuminate.

*Base*.—Truncate.

*Margin*.—Entire.

*Texture*.—Adaxial surface: Puberulent, longitudinally ribbed. Ribs 1 mm apart, minutely raised. Abaxial surface: Glabrous, longitudinal depressions.

*Color*.—N186B.

Flowers:

*Quantity*.—From 4 to 12 flowers per whorl and up to 13 whorls per flowering stem.

*Shape*.—Tubular, two-lipped.

*Length*.—4.5 cm.

*Width*.—8 mm to 10 mm.

*Height* (*across extremities of upper and lower lip*).—2.0 cm.

*Fragrance*.—Slight and pleasant sage fragrance.

Bud (as emerges from calyx):

*Shape*.—Ellipsoidal.

*Length*.—4 mm to 5 mm.

*Width*.—3 mm to 4 mm.

*Texture*.—Pubescent, especially apex which already bears cluster of hairs of upper petal lip.

*Color*.—N186B.

Corolla:

*Shape*.—Tubular.

*Length*.—1.5 cm.

*Width*.—3 mm.

*Texture*.—Glabrous.

*Color* (*both surfaces*).—71A beyond calyx, NN155D and translucent within calyx.

Petals:

*Quantity*.—2.

*Arrangement*.—One upper petal appearing as a hood, and one lower petal which appears as a large prominent lip.

*Upper petal*.—Aspect: Horizontal to slightly elevated. Shape: Hood. Length: 4.5 cm (including corolla tube). Width: 4 mm. Height: 8 mm. Texture: Adaxial surface: Corolla tube glabrous, hood puberulent, hairs 0.5 mm to 1.0 mm in length, hair color 71A. Abaxial surface: Glabrous, with two longitudinal ribs. Apex: Rounded. Base: Truncate with lower lip at corolla mouth. Margin: Smooth, entire. Color (both surfaces): 71A.

*Lower petal, lip*.—Aspect: Downward, between 30° and 45° below horizontal. Shape: Rhomboid, concave. Length: 12 mm to 15 mm (free of upper petal). Width: 7 mm. Texture: Adaxial surface: Smooth. Abaxial surface: Smooth, glabrous, semi-glossy. Apex: Emarginate, shallow curved notch, depth of notch 1 mm. Base: Truncate. Margin: Gently undulating. Color (both surfaces): 71A.

*Floral bracts*.—Absent.

Reproductive organs:

*Stamens*.—Quantity: 2, connected to corolla tube wall, fused at base. Length: 12 cm.

*Filament*.—Length: 10 mm, diameter 1 mm. Color: 71A at base becoming 76D below anthers.

*Anther*.—Shape: Narrowly elliptical, dorsifixed off-center. Length: 3 mm. Width: 0.5 mm to 1.0 mm. Color: N199A.

*Pollen*.—Amount: Sparse. Color: 163B.

*Pistil*.—Quantity: 1. Stigma: Shape: Symmetrically forked, each fork 4 mm in length, recurved. Length: Longer fork 12 mm, strongly recurved; shorter fork 10 mm, gently recurved. Width: 0.5 mm. Color: 71A. Style: Length: 12 mm. Color: 76D.

*Ovary* (*only observed unfertilized, one pair of immature achenes*).—Length: 2.5 mm. Width: 1.5 mm. Color: 11B, achenes 150B.

*Seed*.—Shape: Ovoid. Dimensions: 3 mm in length, 1.5 mm in diameter. Color: 199A to 199B. Surface: Rough.

Disease and pest susceptibility: Susceptible to aphids (*Aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

'Smokey Jazz' is a distinct variety of *Salvia* and is distinguished from its parents as described in Tables 1 and 2.

TABLE 1

Comparison with female parent

| Characteristic | 'Smokey Jazz' | Female Parent 'BBSAL09001' |
|---|---|---|
| Flower color | Red-purple | Violet-blue |
| Peduncle and calyx color | Red-purple | Violet-blue |

TABLE 2

Comparison with male parent

| Characteristic | 'Smokey Jazz' | Male Parent 'Rhythm and Blues' |
|---|---|---|
| Flower color | Red-purple | Violet-blue |
| Flower size | 45 mm | 55 cm to 60 cm |
| Root structure | Non-spreading | Rhizomatous and spreading |
| Time to flower from rooting | Very early; 2 to 3 weeks | 12 weeks |
| Size of leaves | 5.5 cm by 4.0 cm | 9.0 cm by 7.0 cm |

'Smokey Jazz' may also be compared with *Salvia* variety named 'Amistad' (U.S. Plant Pat. No. 23,578) as follows. Differences between the varieties are described in Table 3.

TABLE 3

Comparison with similar variety

| Characteristic | 'Smokey Jazz' | 'Amistad' |
|---|---|---|
| Plant size | 75 cm by 50 cm | 100 cm by 75 cm |
| Flower color | Red-purple | Violet |
| Time to flower from rooting | Very early; 2 to 3 weeks | 2 months |
| Quantity of flowers per inflorescence | Average is 75 | Average is 25 |

I claim:

1. A new and distinct cultivar of *Salvia* plant named 'Smokey Jazz' as described and illustrated herein.

* * * * *